United States Patent [19]

Holtkamp

[11] Plant 5,020

[45] Apr. 5, 1983

[54] AFRICAN VIOLET PLANT

[76] Inventor: Reinhold Holtkamp, Werther Strasse 112, 4294 Isselburg, Fed. Rep. of Germany

[21] Appl. No.: 300,516

[22] Filed: Sep. 9, 1981

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet plant known by the cultivar name Vermont having strong upright stems, with 10–12 flowers per stem, with the flowers being clear and deep blue, the cultivar flowers profusely, has a uniform growth habit, and lush medium green leaves.

1 Drawing Figure

The present invention comprises a new and distinct cultivar of African violet plant, botanically known as *Saintpaulia ionantha,* and hereinafter referred to by the cultivar name Vermont.

The new cultivar was referred to during the breeding and selection process by the designation E 18/1, and is a product of a planned breeding program. The basic objective of the breeding program was to create a new African violet cultivar having single flower form, blue in color, and upright stems with a profuse flower head.

The new cultivar was originated from a cross made in a controlled breeding program in Isselburg, West Germany. The female, or seed parent was a cultivar designated b 296 SAM blue. The male, or pollen parent was a cultivar designated FEDA blue upright.

The new cultivar Vermont was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Vermont has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeated observed and are determined to be basic characteristics of Vermont, which in combination distinguish this African violet as a new and distinct cultivar:

1. Vigorous growth habit.
2. Nine to fifteen strong upright flower stems.
3. Ten to twelve or more flowers per stem.
4. Clear and deep blue blossom color.
5. Profuse flowering.
6. Uniform in growth.
7. Lush medium green leaves.
8. Attractive saleable plant within 8–9 weeks after potting.

The accompanying photographic drawing shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Vermont.

Parentage:

*Male parent.*—FEDA blue upright.

*Female parent.*—b 296 SAM blue.

Propagation: The new cultivar holds its distinguishing characteristics through successive propagations by leaf cuttings and by division of shoots.

Plant: From 9 cm. to 11 cm. tall when grown in pots, and approximately 25 cm. in diameter when fully grown.

Leaves:

*General form.*—Heart-shaped.

*Diameter.*—65 mm.

*Texture.*—Soft and slightly hairy.

*Aspect.*—Shiny.

*Veins.*—Upperside visible; underside well-pronounced and purplish brown, more mature leaves light green.

*Color (upperside).*—HCC parsley green 00962.

*Color (underside).*—HCC willow green 000862/2; older ones sage green 00861/3.

*Petiole.*—Young petiole purplish brown; old petiole brownish green.

Flowers:

*Buds.*—Bell-shaped; 7 mm. just before opening; 10–12 or more per stem.

*Sepals.*—Color: Greenish brown. Calyx: Funneled. Aspect: Spear-shaped, hairy. Peduncle: Short and sturdy, upright, brownish.

Individual flowers:

*Size.*—40–45 mm.

*Color.*—Upperside: Victoria violet 738, center slightly darker, velvety. Underside: Victoria violet 738/2.

*Borne.*—Flower stem carries up to 12 or more flowers on short strong peduncles; flowers normally display an additional sixth small petal in center of blossom.

*Shape.*—Conventional (2 small and 3 large petals), except for additional petal in center.

Flowering time: First flowers appear 7–8 weeks after potting; after 10 weeks full flowering saleable plant.

Reproductive organs:

*Stamens.*—Four anthers (in star-flowers occasionally up to 6), composed of 2 cells, with seed capsule pushed slightly through.

*Anthers.*—HCC empire yellow 603.

*Filaments.*—4 mm. long; light yellowish green.

*Styles.*—7 mm., mineral violet 635; base of ovary light green and hairy.

*Pollen color.*—HCC canary yellow $\frac{2}{3}$.

Roots: White when young and active; greenish brown when older; normally developed.

Disease resistance: Good as experienced to date.

General observations: Vermont is a very vigorous grower with lush medium green leaves and deep blue flower color. It is very rich in blossoms and flowers continuously. Its flowers do not fade and are non-dropping. They are long-lasting and dry off on stem after full maturity.

I claim:

1. A new and distinct cultivar of African violet known by the cultivar name Vermont and particularly characterized by the combined features of vigorous growth habit; 9–15 strong upright flower stems, each of which contains 10–12 or more deep blue flowers; uniform growth habit, and profuse flowering; lush medium green leaves, and by its attractive saleable plant within 8–9 weeks after potting.

* * * * *

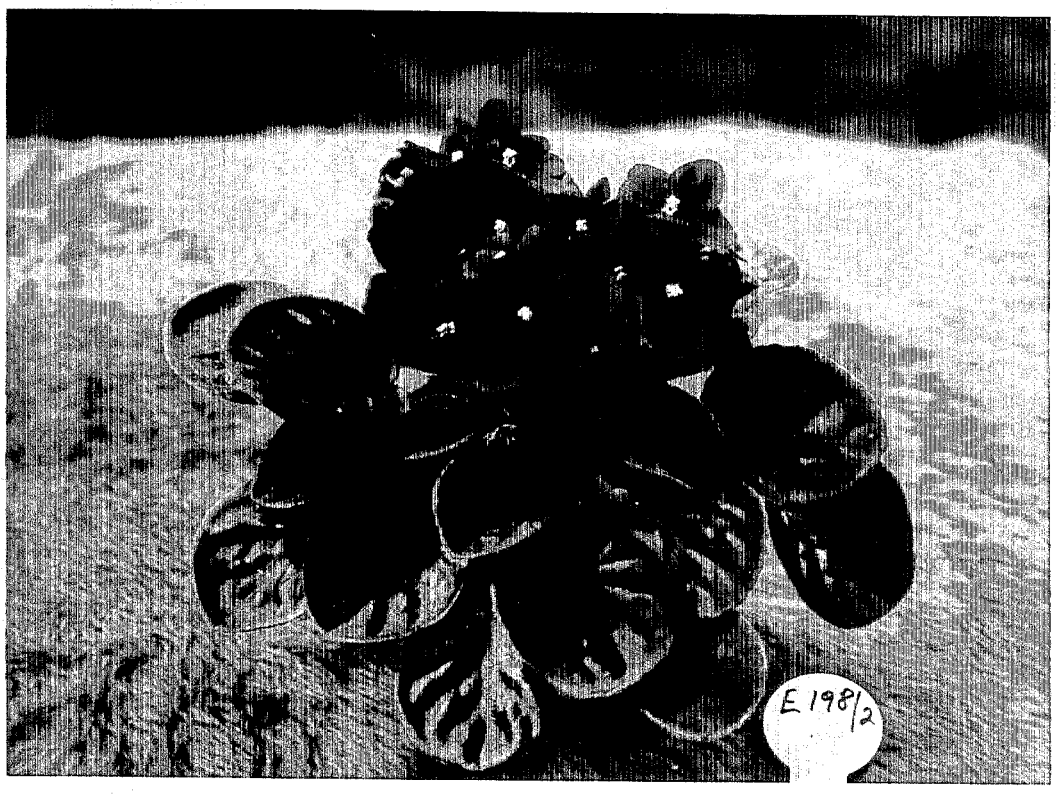
E 198/2

UNITED STATES PATENT AND TRADEMARK OFFICE

CERTIFICATE OF CORRECTION

PATENT NO. : Plant 5,020

DATED : April 5, 1983

INVENTOR(S) : Reinhold Holtkamp

It is certified that error appears in the above-identified patent and that said Letters Patent is hereby corrected as shown below:

On the heading of the colored photographic drawing "Plant 5,020" should read -- Plant 5,025 --, and "Plant 5,025" should read -- Plant 5,020 --.

Signed and Sealed this

*Fifteenth* Day of *April 1986*

[SEAL]

*Attest:*

DONALD J. QUIGG

*Attesting Officer*

*Commissioner of Patents and Trademarks*